United States Patent

Kato et al.

[11] 4,039,635
[45] Aug. 2, 1977

[54] SOIL FUNGICIDAL PHOSPHOROTHIOATE

[75] Inventors: Toshiro Kato, Ibaragi; Mitsuru Sasaki, Nishinomiya; Tadashi Ooishi, Takarazuka; Kunio Mukai, Nishinomiya, all of Japan

[73] Assignee: Sumitomo Chemical Company, Limited, Osaka, Japan

[21] Appl. No.: 642,716

[22] Filed: Dec. 22, 1975

Related U.S. Application Data

[63] Continuation-in-part of Ser. No. 540,546, Jan. 13, 1975, abandoned.

[30] Foreign Application Priority Data

Jan. 29, 1975  Japan .................................. 50-12789

[51] Int. Cl.² .................. C07F 9/165; A01N 9/36
[52] U.S. Cl. ..................................... 260/954; 260/964; 424/218; 424/225
[58] Field of Search ................ 260/954, 964; 424/225, 424/218

[56] References Cited

U.S. PATENT DOCUMENTS

| | | | |
|---|---|---|---|
| 2,599,512 | 6/1952 | Drake et al. | 260/964 |
| 3,107,245 | 10/1963 | Gaunt et al. | 260/964 X |
| 3,322,864 | 5/1967 | Schrader | 260/964 X |
| 3,792,132 | 2/1974 | Bernhart | 260/964 X |

*Primary Examiner*—Anton H. Sutto
*Attorney, Agent, or Firm*—Stevens, Davis, Miller & Mosher

[57] ABSTRACT

Novel phosphorothioates represented by the formula,

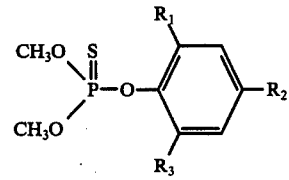

wherein $R_1$ is a chlorine or bromine atom, $R_2$ is methyl or ethyl group and $R_3$ is a chlorine or bromine atom or nitro group, which have a low toxicity to men and beasts as well as fishes, no phytotoxicity to crops, excellent fungicidal effect on injurious epidemic soil fungi in agriculture, horticulture and the like, and a wide range of uses for prevention of soil epidemics to effect the growth promotion of crops.

9 Claims, No Drawings

SOIL FUNGICIDAL PHOSPHOROTHIOATE

This application is a continuation-in-part of application Ser. No. 540,546 filed on Jan. 13, 1975, now abandoned.

This invention relates to a novel organic phosphoric acid ester compound represented by the formula,

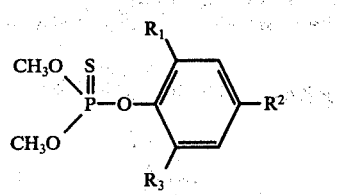

wherein $R_1$ is a chlorine or bromine atom, $R_2$ is a methyl or ethyl group and $R_3$ is a chlorine or bromine atom or nitro group; to a process for preparing the same; and to a soil fungicide containing said compound as an active ingredient.

Plant diseases derived from plant pathogenic fungi, which exist in soil to give great damage to agricultural and horticultural crops by infection, have heretofore been feared as a kind of the most difficultly controllable diseases. Although several soil fungicides are being actually used to control said diseases, these fungicides have no sufficient controlling effects.

On the other hand, environmental pollution due to agricultural chemicals has come to be a serious problem in recent years, and there has strongly been desired the advent of agricultural chemicals which are less toxic to mammals and fishes, do not show phytotoxicity to crops, do not remain in crops and have sufficient controlling effects.

In consideration of the above-mentioned points, the present inventors conducted extensive examinations from various viewpoints on organic phosphoric acid ester compounds. As the result, the inventors have been successful in developing entirely novel soil fungicides which show sufficient controlling effects, are markedly less toxic to mammals and fishes, show no phytotoxicity to crops and do not remain in crops.

The compounds of the present invention have markedly excellent controlling effects on substantially all of soil-borne plant diseases such as damping-off, "Bakanae" disease and sheath blight of rice plants, damping-off of seedlings, and damping-off, Fusarium wilts, yellows, Verticillium wilts, southern blight, rot, late blight of agricultural and horicultural crops. At the same time, the compounds have actions to promote the spread of root portions of crops to make the growth of the crops vigorous, and particularly show prominent effects against damping-off of seedlings and foot rot of crops which are diseases derived from fungi belonging to the genus *Rhizoctonia*. It is needless to say that they have no phytotoxicity on every crop.

On the other hand, the compounds of the present invention are extremely low in toxicity to warm-blooded animals such as mice, rats, dogs and chickens, and fishes such as carps and gold-fishes. Furthermore, the compounds scarcely remain in crops.

The above-mentioned facts indicate that the compounds of the present invention are ideal soil fungicides capable of promoting the growth of agricultural crops without causing any environmental pollution.

The present inventors sufficiently examined in detail the soil-borne disease-controlling effects of many organic phosphoric acid ester compounds, but no effects of controlling soil-borne diseases could be seen even in those which were quite similar in structure to the present compounds.

The compounds disclosed in Australian Pat. No. 294,072 and Ang. Chem., 66 267 (1954), which are prior arts to the present invention, are relatively similar in chemical structure to the present compounds, but did not show any soil-borne disease-controlling effects (refer to Test Examples 1, 2, 3, 4 and 5). Furthermore, 0-2,4,6-trichlorophenyl 0,0-dimethyl thiophosphate disclosed in U.S. Pat. No. 2,599,512 as parasiticides, which compound is quite similar to the present compounds, shows strong neurotoxicity to chickens, and hence cannot be a suitable soil fungicide. On the other hand, the present compounds show no neurotoxicity to chickens at all, and are extremely high in safety.

The excellent controlling effects and low toxicity of the present compounds are ascribable to such specific structure and substituents thereof as represented by the formula (I).

In spite of there existing many organic phosphoric acid ester compounds hitherto, the present inventors have found that only the compounds represented by the formula (I) can show excellent effects of preventing soil-borne diseases. Thus, the present invention, which is based on the above finding, is not only extremely high in inventive idea but also entirely different from the prior art.

The present compounds can be prepared with ease and in high yields by reacting a 2,4,6-trisubstituted phenol represented by the formula,

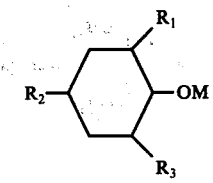

wherein $R_1$ is a chlorine or bormine atom; M is a hydrogen atom, an alkali metal or an ammonium group; $R_2$ is a methyl or ethyl group and $R_3$ is a chlorine or bromine atom or nitro group, with 0,0-dimethylthiophosphoryl chloride preferably in the presence of an acid binding agent and in the presence or absence of a catalyst such as cupper powder and cuprous chloride, or by reacting a salt of said 2,4,6-trisubstituted phenol with 0,0-dimethylthiophosphoryl chloride.

The above-mentioned reaction is preferably carried out in an inert organic solvent, which may be any of, for example, aliphatic or aromatic hydrocarbons (including halides) such as benzene, toluene and chloroform; ethers such as diethyl ether, dioxane and tetrahydrofuran; and aliphatic alcohols and ketones such as methanol, acetone and methylisobutylketone.

Examples of the acid binding agent are sodium hydroxide; potassium hydroxide; alkali metal carbonates and bicarbonates such as potassium carbonate and sodium carbonate; sodium or potassium methylates and ethylates; and aliphatic, aromatic or heterocyclic tertiary bases such as pyridine, triethylamine and N,N-diethylaniline.

Alternatively, the said reaction may be effected by converting the aforesaid 2,4,6-trisubstituted phenol into a salt, preferably an alkali metal or ammonium salt, and then reacting the said salt with 0,0-dimethylthiophosphoryl chloride.

Each of the above-mentioned reactions may be carried out at a temperature in a considerably broad range, but is ordinarily effected at 20° to 110° C., preferably 70° to 100° C. in atmospheric pressure. The reactions may be represented by the following reaction scheme 1:

REACTION SCHEME 1:

nol with phosphorus trichloride at an elevated temperature in the presence of an acid binding agent and an inert solvent, and then with thiophosphoryl trichloride at about room temperature in the presence of an inert solvent to form a 2,4,6-trisubstituted phenyl thiophosphoryl dichloride, and then reacting the said dichloride with sodium or potassium methylate, or with methanol in the presence of an acid binding agent, in the presence of an inert solvent at a temperature ranging from room temperature to the boiling point of the solvent. This reaction may be represented by the following reaction scheme 2:

REACTION SCHEME 2:

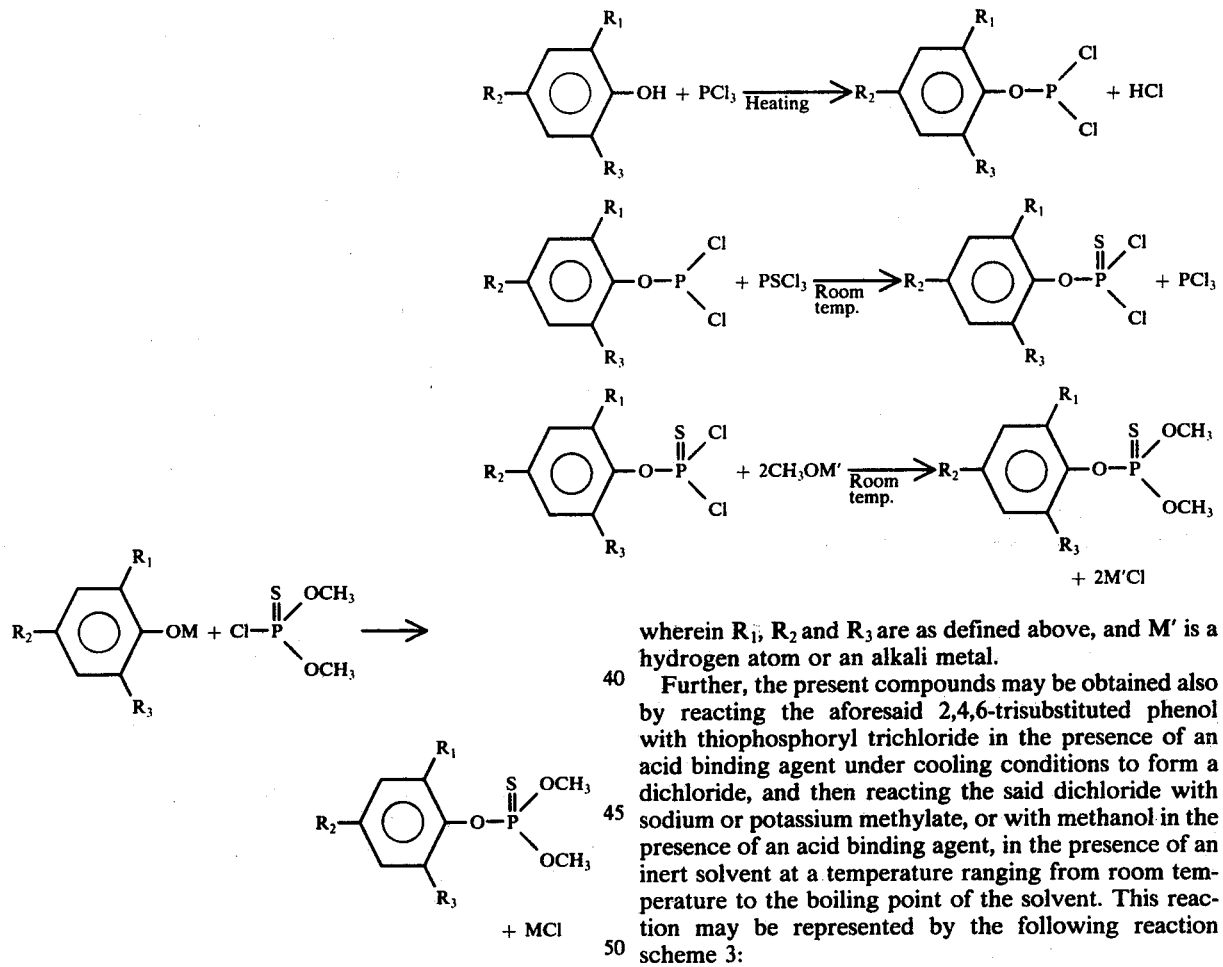

wherein $R_1$, $R_2$ and $R_3$ are as defined above, and M' is a hydrogen atom or an alkali metal.

Further, the present compounds may be obtained also by reacting the aforesaid 2,4,6-trisubstituted phenol with thiophosphoryl trichloride in the presence of an acid binding agent under cooling conditions to form a dichloride, and then reacting the said dichloride with sodium or potassium methylate, or with methanol in the presence of an acid binding agent, in the presence of an inert solvent at a temperature ranging from room temperature to the boiling point of the solvent. This reaction may be represented by the following reaction scheme 3:

wherein $R_1$, $R_2$, $R_3$ and M are as defined previously.

Alternatively, the present compounds may be prepared by reacting the aforesaid 2,4,6-trisubstituted phe-

REACTION SCHEME 3:

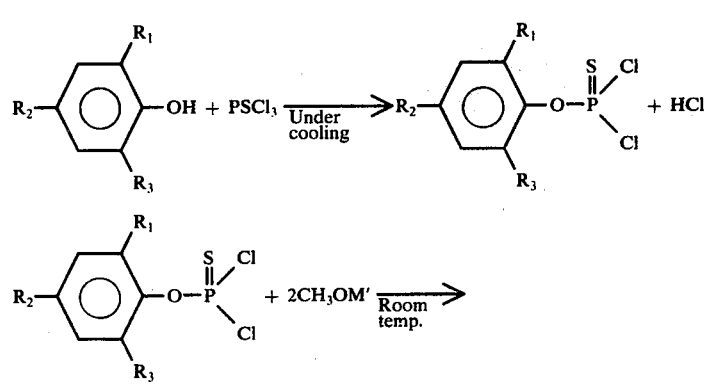

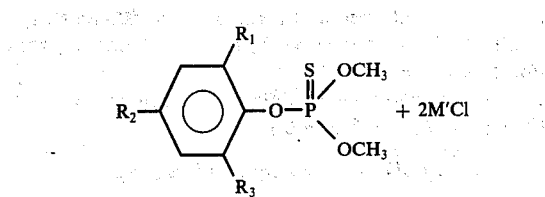 + 2M'Cl wherein $R_1$, $R_2$, $R_3$ and M' are as defined in the reaction scheme 2.

Chemical structures and physical constants of the present compounds are as shown in Table 1.

Table 1

| Compound No. | Chemical structure | Physical constant |
|---|---|---|
| (1) | [2,6-dichloro-4-methylphenyl O,O-dimethyl phosphorothioate] | m.p. 79–79.5° C. |
| (2) | [2-chloro-6-bromo-4-methylphenyl O,O-dimethyl phosphorothioate] | m.p. 73–74° C. |
| (3) | [2,6-dibromo-4-methylphenyl O,O-dimethyl phosphorothioate] | m.p. 81–83° C. |
| (4) | [2,6-dichloro-4-ethylphenyl O,O-dimethyl phosphorothioate] | $n_D^{18.0} = 1.5500$ |
| (5) | [2-chloro-6-bromo-4-ethylphenyl O,O-dimethyl phosphorothioate] | $n_D^{20.0} = 1.5620$ |
| (6) | [2,6-dibromo-4-ethylphenyl O,O-dimethyl phosphorothioate] | $n_D^{20.0} = 1.5672$ |
| (7) | [2-chloro-6-nitro-4-methylphenyl O,O-dimethyl phosphorothioate] | m.p. 78–79° C. |
| (8) | [2-bromo-6-nitro-4-methylphenyl O,O-dimethyl phosphorothioate] | m.p. 73–74° C. |

In actual application, the present compounds may be used as they are or in the form of any conventional preparations such as granules, dusts, fine granules, wettable powders and emulsifiable concentrates. In these preparations, the present compounds may be contained as active ingredients in an amount of 0.1 to about 90%, preferably 5 to 60%. It is desirable that these preparations are used properly according to their application purposes. The preparations may be applied by any such procedure as sprinkling, dusting, spraying, granule-sprinkling, soil-mixing, injection, irrigation, seed dressing and dipping, and prominent fungicidal effects of the preparations can be displayed by adoption of suitable application procedure.

In formulating the above-mentioned preparations, there may be used any of solid carriers, liquid carriers and emulsifiers. Examples of the solid carriers include talc, bentonite, clay, kaolin, diatomaceous earth, vermiculite and slaked lime; examples of the liquid carriers include benzene, alcohols, acetone, xylene, dioxane, methylnaphthalene and cyclohexanone; and examples of the emulsifiers include alkyl sulfuric acid esters, alkyl sulfonates, aryl sulfonates, polyethylene glycol ethers and polyhydric alcohol esters.

When the present compounds are used in admixture with one or more of other fungicides and the resulting compositions are applied in proper forms to soil, effects of controlling soil-borne diseases can be far more increased. Chemicals which can greatly increase the controlling effects when used in admixture with the present compounds are N-trichloromethylthio-tetrahydrophthalimide, sodium p-dimethylaminophenyl-diazosulfonate, 5-ethoxy-3-trichloromethyl-1,2,4-thiadiazole, 5-methyl-3-hydroxy-1,2-oxazole and 1,4-dichloro-2,5-dimethoxybenzene. It is needless to say that the present compounds can be used in admixture also with fungicides other than those mentioned above, insecticides, nematocides, herbicides and fertilizers, and the resulting compositions can greatly contribute to the simultaneous control of diesases and injurious insects and to the promotion of growth of crops.

The present invention is explained in more detail below with reference to examples, but the examples are by way of illustration and not by way of limitation.

EXAMPLE 1 (Compound No. 1):

To a solution of 17.7 g. of 2,6-dichloro-4-methylphenol in 50 ml. of toluene was added 6.9 g. of potassium carbonate. Into the resulting mixture, 16.0 g. of 0,0-dimethylthiophosphoryl chloride was dropped at 50° to 60° C. with stirring. After completion of the dropping, the stirring was further continued at 80° to 85° C. for 3 hours. Thereafter, the reaction liquid was cooled to 20° to 25° C. and then charged with water to separate the liquid into water and toluene layers. The toluene layer was dried with 5 g. of Glauber's salt. Subsequently, the Glauber's salt was separated by filtration, and the toluene was removed by distillation, whereby a solid residue was formed. This residue was recrystallized from methanol to obtain 20.3 g. of white crystals of 0,0-dimethyl 0-2,6-dichloro-4-methylphenyl phosphorothioate having a melting point of 79° to 79.5° C.

EXAMPLE 2 (Compound No. 2):

To a solution of 22.0 g. of 2-bromo-4-methyl-6-chlorophenol in 50 ml. of methyl isobutyl ketone was added 5.3 g. of sodium carbonate. Into the resulting mixture, 16.0 g. of 0,0-dimethylthiophosphoryl chloride was dropped at 70° to 75° C. After completion of the dropping, the mixture was heated with stirring at 100° to 105° C. for 2 hours. Thereafter, the reaction liquid was allowed to cool, and then charged with water to separate the liquid into water and methyl isobutyl ketone layers. Subsequently, the methyl isobutyl ketone was removed by distillation, and the residue was quickly cooled to form a solid. This solid was recrystallized from n-hexane to obtain 18.0 g. of white crystals of 0,0-dimethyl 0-2-bromo-4-methyl-6-chlorophenyl phosphorothioate having a melting point of 73° to 74° C.

EXAMPLE 3 (Compound No. 3):

To a sodium methylate prepared by reaction of 4.6 g. of metallic sodium with 100 ml. of methanol was added 26.4 g. of 2,6-dibromo-4-methylphenol. From the resulting mixture, the methanol was removed by distillation to form a sodium salt of 2,6-dibromo-4-methylphenol. This sodium salt was gradually added to a solution of 16.0 g. of 0,0-dimethylthiophosphoryl chloride in 100 ml. of toluene. After stirring at 90° to 100° C. for 2 hours, the reaction liquid was charged with water to separate the liquid into water and toluene layers. The toluene layer was dried with Glauber's salt. Subsequently the Glauber's salt was separated by filtration and the toluene was removed by distillation, whereby a solid residue was formed. This residue was recrystallized from methanol to obtain 18.0 g. of white crystals of 0,0-dimethyl 0-2,6-dibromo-4-methylphenyl phosphorothioate having a melting point of 81° to 83° C.

EXAMPLE 4 (Compound No. 4):

In the same manner as in Example 1, 0,0-dimethyl 0-2,6-dichloro-4-ethylphenyl phosphorothioate was obtained, $n_D^{18.0} = 1.5500$.

EXAMPLE 5 (Compound No. 5):

In the same manner as in Example 2, 0,0-dimethyl 0-2-bromo-6-chloro-4-ethylphenyl phosphorothioate was obtained, $n_D^{20.0} = 1.5620$.

EXAMPLE 6 (Compound No. 6):

In the same manner as in Example 3, 0,0-dimethyl 0-2,6-dibromo-4-ethylphenyl phosphorothioate was obtained, $n_D^{20.0} = 1.5672$.

(Provided that no recrystallization was required in each of Examples 4, 5 and 6.)

EXAMPLE 7 (Compound No. 1):

17.7 Grams of 2,6-dichloro-4-methylphenol was added to 27.5 g. of phosphorus trichloride with stirring at 20° to 25° C. The resulting mixture was allowed to stand at 75° to 80° C. for 3 hours, and then subjected to fractionation to collect 19.4 g. of fractions having a boiling point of 120° to 125° C. at 0.6 mmHg. The collected fraction was mixed with 16.9 g. of thiophosphoryl trichloride, and the resulting mixture was refluxed for 2 hours. Thereafter, the mixture was fractionated to obtain 28.2 g. of fractions having a boiling point of 90° to 92° C. at 0.01 mmHg. To a solution of said fractions in 300 ml. of toluene, 10.0 g. of sodium methylate was gradually added at 20° to 25° C. After stirring at 20° to 25° C. for 3 hours, the reaction liquid was charged with water to separate the liquid into water and toluene layers. The toluene layer was dried with Glauber's salt. Subsequently, the Glauber's salt was separated by filtration, and the toluene was removed by distillation, whereby a solid residue was formed. The residue was recrystallized from methanol to obtain 23.0 g. of white crystals of 0,0-dimethyl 0-2,6-dichloro-4-methyl-phenyl phosphorothioate having a melting point of 79° to 79.5° C.

EXAMPLE 8 (Compound No. 1):

Into a solution of 28.0 g. of thiophosphoryl trichloride and 17.7 g. of 2,6-dichloro-4-methylphenol in 50 g. of toluene was dropped at 0° to 5° C. 13.3 g. of triethylamine. The resulting mixture was maintained at 20° to 25° C. for 2 hours, and then charged with 50 ml. of a 5% aqueous HCl solution to separate the reaction liquid into water and toluene layers. After washing twice with 50 g. of water, the toluene layer was dried with Glauber's salt. Subsequently, the Glauber's salt was separated by filtration and the toluene was removed by distillation, whereby a solid residue was formed. This residue was subjected to fractionation to collect 25.0 g. of fractions having a boiling point of 90° to 92° C. at 0.01 mmHg. To a solution of said fractions in 300 ml. of toluene, 8.7 g. of sodium methylate was gradually added at 20° to 25° C. After stirring at 20° to 25° C. for 3 hours, the reaction liquid was charged with water to separate the liquid into water and toluene layers. The toluene layer was dried with Glauber's salt. Subsequently, the Glauber's salt was separated by filtration, and the toluene was removed by distillation, whereby a solid residue was formed. This residue was recrystallized from methanol to obtain 14.6 g. of white crystals of 0,0-dimethyl 0-2,6-dichloro-4-methylphenyl phosphorothioate having a melting point of 79° to 79.5° C.

EXAMPLE 9 (Compound No. 7):

To a solution of 18.7 g. of 2-chloro-4-methyl-6-nitrophenol in 50 ml. of toluene was added 6.9 g. of potassium carbonate. Into the resulting mixture, 16.0 g. of 0,0-dimethylthiophosphoryl chloride was dropped at 50° to 60° C. with stirring. After completion of the dropping, the stirring was further continued at 80° to 85° C. for 3 hours. Thereafter, the reaction liquid was cooled to 20° to 25° C. and then charged with water to separate the liquid into water and toluene layers. The toluene layer was dried with 5 g. of Glauber's salt. Subsequently, the Glauber's salt was separated by filtration, and the toluene was removed by distillation, whereby a solid residue was formed. This residue was recrystallized from methanol to obtain 18.0 g. of white crystals of 0,0-dimethyl 0-2-chloro-4-methyl-6-nitrophenyl phosphorothioate having a melting point of 78° to 79° C.

EXAMPLE 10 (Compound No. 8):

To a solution of 23.2 g. of 2-bromo-4-methyl-6-nitrophenol in 50 ml. of methyl isobutyl ketone was added 5.3 g. of sodium carbonate. Into the resulting mixture, 16.0 g. of 0,0-dimethylthiophosphoryl chloride was dropped at 70° to 75° C. After completion of the dropping, the mixture was heated with stirring at 100° to 105° C. for 2 hours. Thereafter, the reaction liquid was allowed to cool, and then charged with water to separate the liquid into water and methyl isobutyl ketone layers. Subsequently, the methyl isobutyl ketone was removed by distillation, and the residue was quickly cooled to form a solid. This solid was recrystallized from n-hexane to obtain 20.5 g. of white crystals of 0,0-dimethyl 0-2-bromo-4-methyl-6-nitrophenyl phosphorothioate having a melting point of 73° to 74° C.

EXAMPLE 11 (Compound No. 8):

To a sodium methylate prepared by reaction of 2.3 g. of metallic sodium with 50 ml. of methanol was added 23.2 g. of 2-bromo-4-methyl-6-nitrophenol. This sodium salt was gradually added to a solution of 16.0 g. of 0,0-dimethylthiophosphoryl chloride in 100 ml. of toluene. After stirring at 90° to 100° C. for 2 hours, the reaction liquid was charged with water to separate the liquid into water and toluene layers. The toluene layer was dried with Glauber's salt. Subsequently the Glauber's salt was separated by filtration and the toluene was removed by distillation, whereby a solid residue was formed. This residue was recrystallized from methanol to obtain 21.0 g. of white crystals of 0,0-dimethyl 0-2-bromo-4-methyl-6-nitrophenyl phosphorothioate having a melting point of 73° to 74° C.

EXAMPLE 12 (Compound No. 7):

18.7 Grams of 2-chloro-4-methyl-6-nitrophenol was added to 27.5 g. of phosphorus trichloride with stirring at 20° to 25° C. The resulting mixture was allowed to stand at 75° to 80° C. for 3 hours, and then subjected to fractionation to collect 20.4 g. of fractions having a boiling point of 140° to 145° C. at 0.5 mmHg. The collected fraction was mixed with 16.9 g. of thiophosphoryl trichloride, and the resulting mixture was refluxed for 2 hours. Thereafter, the mixture was fractionated to obtain 29.2 g. of fractions having a boiling point of 100° to 102° C. at 0.01 mmHg. To a solution of said fractions in 300 ml. of toluene, 10.0 g. of sodium methylate was gradually added at 20° to 25° C. After stirring at 20° to 25° C. for 3 hours, the reaction liquid was charged with water to separate the liquid into water and toluene layers. The toluene layer was dried with Glauber's salt. Subsequently, the Glauber's salt was separated by filtration, and the toluene was removed by distillation, whereby a solid residue was formed. The residue was recrystallized from methanol to obtain 20.5 g. of white crystals of 0,0-dimethyl0-2-chloro-4-methyl-6-nitrophenyl phosphorothioate having a melting point of 78° to 79° C.

EXAMPLE 13 (Compound No. 7):

Into a solution of 28.0 g. of thiophosphoryl trichloride and 18.7 g. of 2-chloro-4-methyl-6-nitrophenol in 50 g. of toluene was dropped at 0° to 5° C. 13.3 g. of triethylamine. The resulting mixture was maintained at 20° to 25° C. for 2 hours, and then charged with 50 ml. of a 5% aqueous HCl solution to separate the reaction liquid into water and toluene layers. After washing twice with 50 g. of water, the toluene layer was dried with Gluaber's salt. Subsequently, the Glauber's salt was separated by filtration and the toluene was removed by distillation, whereby a solid residue was formed. This residue was subjected to fractionation to collect 25.0 g. of fractions having a boiling point of 100° to 102° C. at 0.01 mmHg. To a solution of said fractions in 300 ml. of toluene, 8.7 g. of sodium methylate was gradually added at 20° to 25° C. After stirring at 20° to 25° C. After stirring at 20° to 25° C. for 3 hours, the reaction liquid was charged with water to separate the liquid into water and toluene layers. The toluene layer was dried with Glauber's salt. Subsequently, the Glauber's salt was separated by filtration, and the toluene was removed by distillation, whereby a solid residue was formed. This residue was recrystallized from methanol to obtain 14.5 g. of white crystals of 0,0-dimethyl 0-2-chloro-4-methyl-6-nitrophenyl phosphorothioate having a melting point of 78° to 79° C.

Procedures for compounding the present compounds into fungicidal compositions are explained in detail below with reference to compounding examples, but the kinds and proportions of additives for the present compounds are variable within broad scopes without being limited to those shown in the examples. In the examples, all the parts are by weight.

COMPOUNDING EXAMPLE 1 DUST:

A mixture comprising 10 parts of the present compound (1) and 90 parts of clay was sufficiently pulverized to obtain a dust containing 10% of active ingredient. In application, the dust was dusted as it was or thoroughly kneaded with soil.

COMPOUNDING EXAMPLE 2 WETTABLE POWDER:

A mixture comprising 50 parts of the present compound (4), 5 parts of a wetting agent (alkylbenzenesulfonate type) and 45 parts of diatomaceous earth was sufficiently pulverized to obtain a wettable powder containing 50% of active ingredient. In application, the wettable powder was diluted with water, and the resulting dilution was irrigated into water.

COMPOUNDING EXAMPLE 3 EMULSIFIABLE CONCENTRATE:

A mixture comprising 20 parts of the present compound (3), 60 parts of xylene and 20 parts of an emulsifier (polyoxyethylene phenylphenol polymer type) was sufficiently kneaded to obtain an emulsifiable concentrate containing 20% of active ingredient. In application, the concentrate was diluted with water, and the resulting emulsion was irrigated into soil.

COMPOUNDING EXAMPLE 4 GRANULE:

A mixture comprising 10 parts of the present compound (5), 85 parts of silica powder, 4.95 parts of calcium lignin sulfate and 0.05 parts of sodium alkylbenzenesulfonate was sufficiently pulverized, kneaded with water, granulated, and then dried to obtain a granule containing 10% of active ingredient. In application, the granule was sprinkled as it was or kneaded with soil.

COMPOUNDING EXAMPLE 5 COMPOUND DUST:

A mixture comprising 2 parts of the present compound (1), 3 parts of N-trichloromethylthio tetrahydrophthalimide and 95 parts of talc was sufficiently pulverized to obtain a compounded dust containing 5% of active ingredient.

COMPOUNDING EXAMPLE 6 COMPOUNDED DUST:

A mixture comprising 2 parts of the present compound (6), 3 parts of sodium paradimethylaminophenyl diazosulfonate and 95 parts of clay was sufficiently pulverized to obtain a compounded dust containing 5% of active ingredient.

COMPOUNDING EXAMPLE 7 COMPOUNDED DUST:

A mixture comprising 2 parts of the present compound (4), 3 parts of 5-ethoxy-3-trichloromethyl-1,2,4-thiadiazole and 95 parts of clay was sufficiently pulverized to obtain a compounded dust containing 5% of active ingredient.

COMPOUNDING EXAMPLE 8 COMPOUNDED DUST:

A mixture comprising 2 parts of the present compound (1), 1 part of 5-methyl-3-hydroxy-1,2-oxazole and 97 parts of clay was sufficiently pulverized to obtain a compounded dust containing 3% of active ingredient.

COMPOUNDING EXAMPLE 9 COMPOUNDED DUST:

A mixture comprising 2 parts of the present compound (5), 8 parts of 1,4-dichloro-2,5-dimethoxybenzene and 90 parts of clay was sufficiently pulverized to obtain a compounded dust containing 10% of active ingredient.

COMPOUNDING EXAMPLE 10 DUST:

A mixture comprising 10 parts of the present compound (7) and 90 parts of clay was sufficiently pulverized to obtain a dust containing 10% of active ingredient. In application, the dust was dusted as it was or thoroughly kneaded with soil.

COMPOUNDING EXAMPLE 11 WETTABLE POWDER:

A mixture comprising 50 parts of the present compound (8), 5 parts of a wetting agent (alkylbenzenesulfonate type) and 45 parts of diatomaceous earth was sufficiently pulverized to obtain a wettable powder containing 50% of active ingredient. In application, the wettable powder was diluted with water, and the resulting dilution was irrigated into water.

COMPOUNDING EXAMPLE 12 EMULSIFIABLE CONCENTRATE:

A mixture comprising 20 parts of the present compound (7), 60 parts of xylene and 20 parts of an emulsifier (polyoxyethylene phenylphenol polymer type) was sufficiently kneaded to obtain an emulsifiable concentrate containing 20% of active ingredient. In application, the concentrate was diluted with water, and the resulting emulsion was irrigated into soil.

COMPOUNDING EXAMPLE 13 GRANULE:

A mixture comprising 10 parts of the present compound (7), 85 parts of silica powder, 4.95 parts of calcium lignin sulfate and 0.05 part of sodium alkylbenzenesulfonate was sufficiently pulverized, kneaded with water, granulated, and then dried to obtain a granule containing 10% of active ingredient. In application, the granule was sprinkled as it was or kneaded with soil.

COMPOUNDING EXAMPLE 14 COMPOUNDED DUST:

A mixture comprising 2 parts of the present compound (8), 3 parts of N-trichloromethylthio tetrahydrophthalimide and 95 parts of talc was sufficiently pulverized to obtain a compounded dust containing 5% of active ingredient.

COMPOUNDING EXAMPLE 15 COMPOUNDED DUST:

A mixture comprising 2 parts of the present compound (8), 3 parts of sodium paradimethylaminophenyl diazosulfonate and 95 parts of clay was sufficiently pulverized to obtain a compounded dust containing 5% of active ingredient.

COMPOUNDING EXAMPLE 16 COMPOUNDED DUST:

A mixture comprising 2 parts of the present compound (7), 3 parts of 5-ethoxy-3-trichloromethyl-1,2,4-thiadiazole and 95 parts of clay was sufficiently pulverized to obtain a compounded dust containing 5% of active ingredient.

COMPOUNDING EXAMPLE 17 COMPOUNDED DUST:

A mixture comprising 2 parts of the present compound (7), 1 part of 5-methyl-3-hydroxy-1,2-oxazole and 97 parts of clay was sufficiently pulverized to obtain a compounded dust containing 3% of active ingredient.

COMPOUNDING EXAMPLE 18 COMPOUNDED DUST:

A mixture comprising 2 parts of the present compound (7), 8 parts of 1,4-dichloro-2,5-dimethoxybenzene and 90 parts of clay was sufficiently pulverized to obtain a compounded dust containing 10% of active ingredient.

In order to substantiate excellent soil fungicidal effects of the present compounds, typical test results are described below with reference to test examples, but the test examples are part of typical tests, and it is needless to say that the present compounds have extremely broad application scopes as soil fungicides.

TEST EXAMPLE 1

Cucumber damping-off-controlling effect (Pot test):
Farm soil was filled in 9 cm-diameter flower pots. On the surface of said soil was uniformly spread and inoculated 10 ml. per pot of pathogenic soil in which *Rhizoctonia solani* had been cultured. Subsequently, each of aqueous dilutions of test chemicals in the form of emulsifiable concentrates was irrigated into the thus treated soil in a proportion of 15 ml. per pot. After 2 hours, 10 seeds per pot of cucumber (variety: Kaga-Aonagafushinari) were sowed in soil and, 5 days thereafter, the disease severity of cucumber seedlings was investigated to calculate the percentage of healthy seedlings. The said percentage was calculated according to the following formula:

$$\text{Percentage of healthy seedlings} = \frac{\text{Number of healthy seedlings in treated area}}{\text{Number of germinated seeds in non-treated and non-inoculated area}} \times 100 \,(\%)$$

As the result, the present compounds showed markedly excellent effects over the control similar compounds as shown in Table 2.

Table 2

| Compound | Active ingredient concentration (p.p.m) | Percentage of healthy seedlings (%) |
|---|---|---|
| Compound No. (1): (CH₃O)₂P(=S)—O—(2,6-dichloro-4-methylphenyl) | 250 / 125 / 62.5 | 100 / 100 / 90 |
| Compound No. (2): (CH₃O)₂P(=S)—O—(2-chloro-6-bromo-4-methylphenyl) | 250 / 125 / 62.5 | 100 / 100 / 70 |
| Compound No. (3): (CH₃O)₂P(=S)—O—(2,6-dibromo-4-methylphenyl) | 250 / 125 / 62.5 | 100 / 100 / 60 |
| Compound No. (4): (CH₃O)₂P(=S)—O—(2,6-dichloro-4-ethylphenyl) | 250 / 125 / 62.5 | 100 / 100 / 80 |
| Compound No. (5): (CH₃O)₂P(=S)—O—(2-chloro-6-bromo-4-ethylphenyl) | 250 / 125 / 62.5 | 100 / 90 / 60 |
| Compound No. (6): (CH₃O)₂P(=S)—O—(2,6-dibromo-4-ethylphenyl) | 250 / 125 / 62.5 | 100 / 90 / 50 |

Table 2-continued

| Compound | Active ingredient concentration (p.p.m) | Percentage of healthy seedlings (%) |
|---|---|---|
| Compound No. (7): (CH₃O)₂P(=S)—O—(2-chloro-6-nitro-4-methylphenyl) | 250 / 125 | 100 / 100 |
| Compound No. (8): (CH₃O)₂P(=S)—O—(2-bromo-6-nitro-4-methylphenyl) | 250 / 125 | 100 / 100 |
| (C₂H₅O)₂P(=S)—O—(2-chloro-6-nitro-4-methylphenyl) * | 500 | 10 |
| (C₂H₅O)₂P(=S)—O—(2-bromo-6-nitro-4-methylphenyl) * | 500 | 0 |
| (CH₃O)₂P(=O)—O—(2-bromo-6-nitro-4-methylphenyl) * | 500 | 0 |
| (CH₃O)₂P(=S)—O—(2,6-dichloro-4-nitrophenyl) (****) | 500 | 0 |
| (CH₃O)₂P(=S)—O—(2-methyl-3-chloro-4-nitrophenyl) (****) | 500 | 0 |
| (CH₃O)₂P(=S)—O—(2-methyl-6-chloro-4-nitrophenyl) (****) | 500 | 0 |
| (CH₃O)₂P(=S)—O—(2-chloro-4-nitro-5-methylphenyl) (****) | 500 | 0 |

Table 2-continued

| Compound | Active ingredient concentration (p.p.m) | Percentage of healthy seedlings (%) |
|---|---|---|
| $(CH_3)_2P(=O)-O-$[2,6-dichloro-4-methylphenyl]  * | 250 | 10 |
| $(C_2H_5O)_2P(=S)-O-$[2,6-dichloro-4-methylphenyl]  * | 250 | 10 |
| $(CH_3O)_2P(=S)-O-$[2,4,6-trichlorophenyl]  * | 250 | 0 |
| $(CH_3O)_2P(=S)-O-$[2,4-dichlorophenyl]  * | 250 | 20 |
| $C_2H_5, CH_3O$ - $P(=O)-O-$[2,4-dichlorophenyl]  ** | 500 / 250 | 0 / 0 |
| $CH_3, C_2H_5O$ - $P(=O)-O-$[2,4,6-trichlorophenyl]  ** | 500 / 250 | 0 / 0 |
| $CH_3O, iC_3H_7O$ - $P(=O)-O-$[2,4,6-trichlorophenyl]  ** | 500 / 250 | 0 / 0 |
| $(C_2H_5O)_2P(=S)-O-$[2,6-dibromo-4-chloro-3-methylphenyl]  ** | 500 / 250 | 0 / 0 |
| $(CH_3O)_2P(=S)-O-$[4-nitro-3-(methylthiomethyl)phenyl]  ** | 500 / 250 | 0 / 0 |
| $(C_2H_5O)_2P(=S)-SCH_3$  *** | 250 | 0 |
| 2,3,4,5,6-pentachloro-nitrobenzene (Cl / Cl / Cl / Cl / NO_2)  ***** | 500 / 250 | 80 / 30 |
| Fungus inoculated, Non-treatment | — | 0 |
| Non-inoculation, Non-treatment | — | 100 |

Notes:
* Control compounds synthesized for comparison by the present inventors.
** Compounds disclosed in Australian Patent 294,072.
*** Compound disclosed in Belgian Patent 648,813.
**** Compound disclosed in Aug. Chem., 66 267 (1954).
***** Commercially available soil fungicide.
(The same shall apply hereinafter.)

TEST EXAMPLE 2

Cucumber damping-off controlling effect (Vat test):

Farm soil was filled in plastic-made vats of 0.1 m² in size. On the surface of said soil was uniformly spread and inoculated pathogenic soil in which *Rhizoctonia solani* had been cultured, and the pathogenic soil was sufficiently mixed with the farm soil to a depth of 3 to 5 cm from its surface. Subsequently, each of aqueous dilutions of test chemicals in the form of emulsifiable concentrates was irrigated into the thus treated soil in a proportion of 300 ml. per vat. After 2 hours, 30 seeds per vat of cucumber (variety: Kage-Aonagafushinari) were sowed in the soil and, one month thereafter, the disease severity of cucumber seedlings was investigated to calculate the percentage of healthy seedlings. The said percentage was calculated according to the same formula as in Test Example 2.

As the results, the present compounds showed markedly excellent controlling effects over the control similar compounds as shown in Table 3.

Table 3

| Compound | Active ingredient concentration (p.p.m) | Percentage of healthy seedlings (%) |
|---|---|---|
| $(CH_3O)_2P(=S)-O-$[2,6-dichloro-4-methylphenyl] — Compound No. (1) | 200 | 98 |
| $(CH_3O)_2P(=S)-O-$[2-chloro-6-bromo-4-methylphenyl] — Compound No. (2) | 200 | 98 |

Table 3-continued
| Compound | Active ingredient concentration (p.p.m) | Percentage of healthy seedlings (%) |
|---|---|---|
| 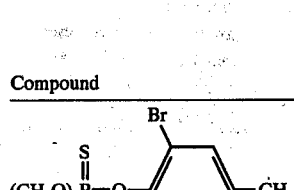 Compound No. (3) | 200 | 97 |
| 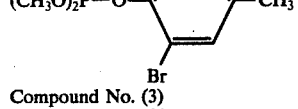 Compound No. (4) | 200 | 97 |
| 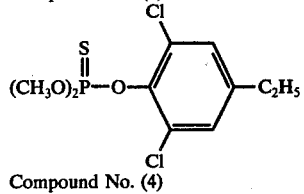 Compound No. (5) | 200 | 97 |
| 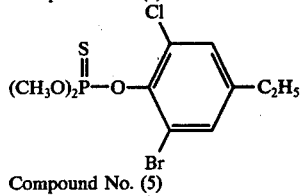 Compound No. (6) | 200 | 95 |
| 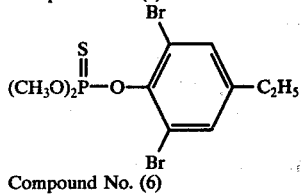 Compound No. (7) | 200 | 100 |
| 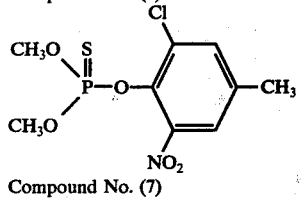 Compound No. (8) | 200 | 100 |
| 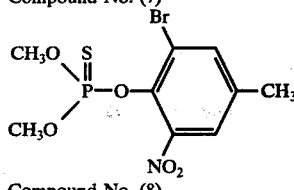 | * 500 | 8.9 |
| 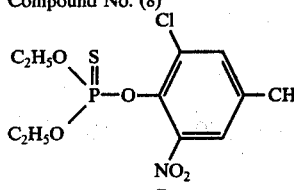 | * 500 | 0 |
| 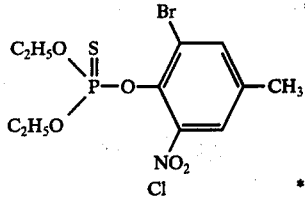 | * 500 | 0 |
| 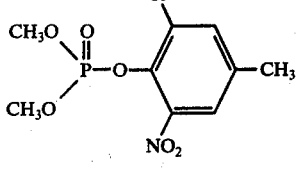 | * 500 | 0 |
|  | **** 500 | 0 |
| 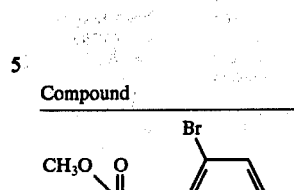 | **** 500 | 0 |
| 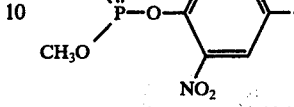 | **** 500 | 0 |
| 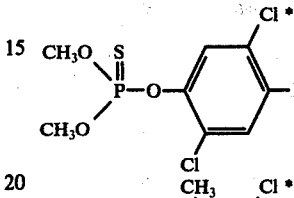 | **** 500 | 0 |
| 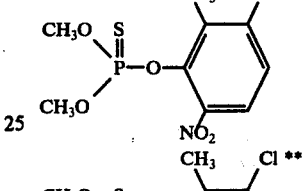 | * 200 | 8 |
| 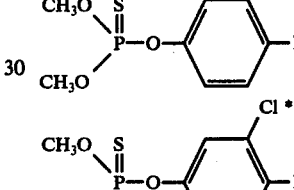 | * 200 | 5 |
| 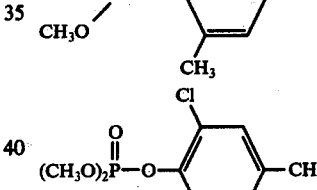 | * 200 | 3 |
| 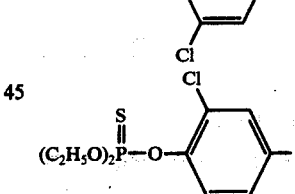 | * 200 | 8 |
| 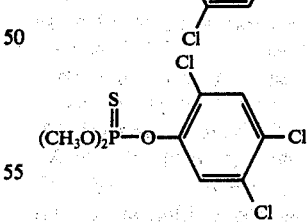 | ** 500 200 | 0 0 |

Table 3-continued

| Compound | Active ingredient concentration (p.p.m) | Percentage of healthy seedlings (%) |
|---|---|---|
| $CH_3$ \ $\overset{O}{\underset{\|}{P}}$ / $C_2H_5O$ —O—(2,4,5-Cl_3-C_6H_2)** | 500<br>200 | 6.7<br>2 |
| $CH_3O$ \ $\overset{O}{\underset{\|}{P}}$ / $iC_3H_7O$ —O—(2,4,5-Cl_3-C_6H_2)** | 500<br>200 | 0<br>0 |
| $(C_2H_5O)_2\overset{S}{\underset{\|}{P}}$—O—(2-Br-4-Cl-6-Br-3-CH_3-C_6H)** | 500<br>200 | 0<br>0 |
| $(CH_3O)_2\overset{S}{\underset{\|}{P}}$—O—(2-CH_2SCH_3-4-NO_2-C_6H_3)** | 500<br>200 | 13.3<br>8 |
| $(C_2H_5O)_2$—$\overset{S}{\underset{\|}{P}}$—SCH_3*** | 200 | 0 |
| (2,3,4,6-Cl_4-5-NO_2-C_6)***** | 500<br>200 | 53.3<br>36 |
| Fungus inoculated, Non-treatment | — | 0 |
| Non-inoculation, Non-treatment | — | 98 |

TEST EXAMPLE 3

Japanese raddish Fusarium wilt-controlling effect (Vat test):

Farm soil was filled in plastic-made vats of 0.1 m² in size. Subsequently, pathogenic soil, in which *Fusarium oxysporum f. raphani* had been cultured, was mixed with and inoculated into the farm soil to a depth of 5 cm. from the surface thereof. On the thus treated soil, 30 seeds per pot of Japanese raddish (variety: Wase 40-nichi) were sowed, and the seeds were covered with soil. After 3 hours, each of aqueous dilutions of test chemicals in the form of emulsifiable concentrates was irrigated into the soil in a proportion of 300 ml. per vat. After culturing the raddish for one month in an air-controlled greenhouse at 26° to 28° C., the disease severity of raddish seedlings was investigated to calculate the percentage of healthy seedlings. The said percentage was calculated according to the same formula as in Test Example 1.

As the result, the present compounds showed markedly excellent controlling effects over the control compounds as shown in Table 4.

Table 4

| Compound | Active ingredient concentration (p.p.m) | Percentage of healthy seedlings (%) |
|---|---|---|
| $(CH_3O)_2\overset{S}{\underset{\|}{P}}$—O—(2,6-Cl_2-4-CH_3-C_6H_2)<br>Compound No. (1) | 500 | 98 |
| $(CH_3O)_2\overset{S}{\underset{\|}{P}}$—O—(2-Cl-6-Br-4-CH_3-C_6H_2)<br>Compound No. (2) | 500 | 95 |
| $(CH_3O)_2\overset{S}{\underset{\|}{P}}$—O—(2,6-Br_2-4-CH_3-C_6H_2)<br>Compound No. (3) | 500 | 97 |
| $(CH_3O)_2\overset{S}{\underset{\|}{P}}$—O—(2,6-Cl_2-4-C_2H_5-C_6H_2)<br>Compound No. (4) | 500 | 92 |
| $(CH_3O)_2\overset{S}{\underset{\|}{P}}$—O—(2-Cl-6-Br-4-C_2H_5-C_6H_2)<br>Compound No. (5) | 500 | 95 |
| $(CH_3O)_2\overset{S}{\underset{\|}{P}}$—O—(2,6-Br_2-4-C_2H_5-C_6H_2)<br>Compound No. (6) | 500 | 97 |
| $CH_3O$ \ $\overset{S}{\underset{\|}{P}}$ / $CH_3O$ —O—(2-Cl-6-NO_2-4-CH_3-C_6H_2)<br>Compound No. (7) | 500 | 100 |
| $CH_3O$ \ $\overset{S}{\underset{\|}{P}}$ / $CH_3O$ —O—(2-Br-6-NO_2-4-CH_3-C_6H_2)<br>Compound No. (8) | 500 | 100 |

Table 4-continued

| Compound | Active ingredient concentration (p.p.m) | Percentage of healthy seedlings (%) |
|---|---|---|
| (C₂H₅O)₂P(=S)−O−[2-Cl,4-CH₃,6-NO₂-C₆H₂] * | 500 | 5.6 |
| (C₂H₅O)₂P(=S)−O−[2-Br,4-CH₃,6-NO₂-C₆H₂] * | 500 | 7.8 |
| (CH₃O)₂P(=O)−O−[2-Cl,4-CH₃,6-NO₂-C₆H₂] * | 500 | 12.2 |
| (CH₃O)₂P(=O)−O−[2-Br,4-CH₃,6-NO₂-C₆H₂] * | 500 | 11.1 |
| (CH₃O)₂P(=S)−O−[2,5-Cl₂,4-NO₂-C₆H₂] **** | 500 | 3.3 |
| (CH₃O)₂P(=S)−O−[2-CH₃,3-Cl,4-NO₂-C₆H₂] **** | 500 | 6.7 |
| (CH₃O)₂P(=S)−O−[2-CH₃,3-Cl,4-NO₂-C₆H₂] **** | 500 | 8.9 |
| (CH₃O)₂P(=S)−O−[3-Cl,4-NO₂,6-CH₃-C₆H₂] **** | 500 | 4.4 |
| (CH₃O)₂P(=O)−O−[2,6-Cl₂,4-CH₃-C₆H₂] * | 500 | 8 |
| (C₂H₅O)₂P(=S)−O−[2,6-Cl₂,4-CH₃-C₆H₂] * | 500 | 10 |
| (CH₃O)₂P(=S)−O−[2,4,5-Cl₃-C₆H₂] * | 500 | 12 |
| (CH₃O)₂P(=S)−O−[2,4-Cl₂-C₆H₃] * | 500 | 14 |
| (C₂H₅)(CH₃O)P(=O)−O−[2,4-Cl₂-C₆H₃] ** | 500 | 8 |
| (CH₃)(C₂H₅O)P(=O)−O−[2,4,5-Cl₃-C₆H₂] ** | 500 | 15 |
| (CH₃O)(iC₃H₇O)P(=O)−O−[2,4,5-Cl₃-C₆H₂] ** | 500 | 14 |
| (C₂H₅O)₂P(=O)−O−[2,6-Br₂,4-Cl,5-CH₃-C₆H] ** | 500 | 10 |
| (CH₃O)₂P(=S)−O−[4-NO₂,2-CH₂SCH₃-C₆H₃] ** | 500 | 12 |
| (C₂H₅O)₂P(=S)−SCH₃ *** | 500 | 7 |
| Benzimidazole: 1-CONH-n-C₄H₉, 2-NHCOOCH₃ ***** | 500 | 78 |
| Fungus inoculated, Non-treatment | — | 7 |
| Non-inoculation, Non-treatment | — | 98 |

TEST EXAMPLE 4

Controlling effect on sheath blight of rice plant:

Each of the test compounds in the form of emulsifiable concentrates was diluted with water and applied to rice plants, which had been cultured in pots of 9 cm. in diameter and grown up to 50–60 cm. in height, in a proportion of 10 ml. of the dilution per pot. After 3 hours, a mycelium-discinoculum of *Pellicularia sasakii* was applied onto the sheaths. 5 Days thereafter, the infectious state of the sheaths was observed, and the degree of damage was calculated according to the following equation:

$$\text{Degree of damage} = \frac{\Sigma \left( \begin{array}{c} \text{Infection} \\ \text{index} \end{array} \times \begin{array}{c} \text{Number of} \\ \text{stems} \end{array} \right)}{\text{Total number of stems} \times 3} \times 100$$

wherein the infection index was determined on the basis of the following criteria:

| Infection index | Infectious state |
|---|---|
| 0 | No infectious spots on the sheaths. |
| 1 | Infectious spot-like shades. |
| 2 | Infectious spots of less than 3 cm. in size. |
| 3 | Infectious spots of not less than 3 cm. in size. |

As the result, the present compounds showed markedly excellent effects over the control similar compounds as shown Table 5.

Table 5

| Compound | Active ingredient concentration (p.p.m) | Degree of damage |
|---|---|---|
| 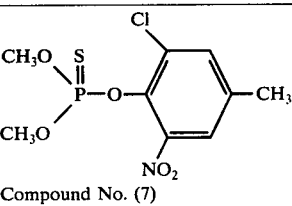 Compound No. (7) | 200 | 0 |
| 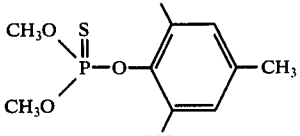 Compound No. (8) | 200 | 0 |
| 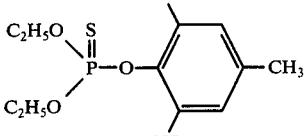 * | 200 | 76.7 |
| 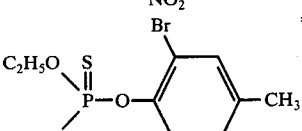 * | 200 | 70 |

Table 5-continued

| Compound | Active ingredient concentration (p.p.m) | Degree of damage |
|---|---|---|
| 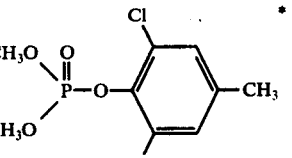 * | 200 | 100 |
| 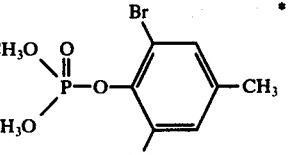 * | 200 | 100 |
| 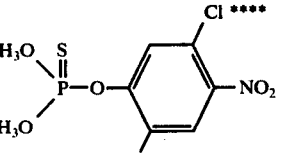 **** | 200 | 100 |
| 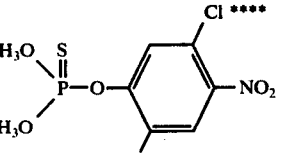 **** | 200 | 100 |
| 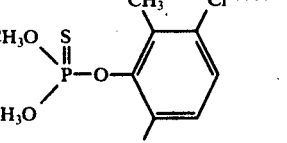 **** | 200 | 100 |
| 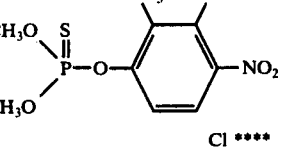 **** | 200 | 100 |
| 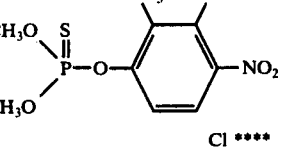 ** | 200 | 100 |
| 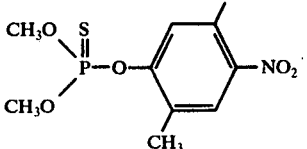 ** | 200 | 100 |
| 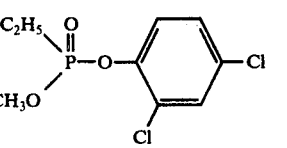 ** | 200 | 100 |

Table 5-continued

| Compound | Active ingredient concentration (p.p.m) | Degree of damage |
|---|---|---|
| (C$_2$H$_5$O)$_2$P(=O)—O—[2,5-dibromo-4-chloro-3-methylphenyl] ** | 200 | 100 |
| (CH$_3$O)$_2$P(=S)—O—[phenyl-NO$_2$, CH$_2$—SCH$_3$] ** | 200 | 100 |
| (CH$_3$O)$_2$P(=S)—O—[2,6-dichloro-4-methylphenyl] — Compound No. (1) | 200 | 16.7 |
| (CH$_3$O)$_2$P(=S)—O—[2-bromo-6-chloro-4-methylphenyl] — Compound No. (2) | 200 | 23.3 |
| TUZ | 200 | 6.7 |
| Untreated | — | 100 |

Note:
TUZ is a commercially available fungicide which contains 40% by weight of tetramethylthiuram disulfide, 20% by weight of methylarsine bis(dimethyldithiocarbamate) and 20% by weight of zinc dimethyldithiocarbamate.

TEST EXAMPLE 5

Controlling effect on southern blight of Kidney been (Pot test):

Farm soil was filled in 11 cm.-diameter flower pots. On the surface of said soil was uniformly spread and inoculated 3 g. per pot of pathogenic soil in which *Corticium rolfsii* had been cultured for 9 days. Subsequently, each of aqueous dilutions of test chemicals in the form of emulsifiable concentrates was irrigated into the thus treated soil in a proportion of 38 ml. per pot. After 2 hours, 5 seeds per pot of Kidney bean (variety: Nagauzura) were sowed in the soil and, 20 days thereafter, the disease severity of Kidney bean seedlings was investigated to calculate the percentage of healthy seedlings. The said percentage was calculated according to the following formula:

$$\text{Percentage of healthy seedlings} = \frac{\text{Number of healthy seedlings in treated plot}}{\text{Number of germinated seeds in non-treated and non-inoculated plot}} \times 100\ (\%)$$

As the result, the present compounds showed markedly excellent effects over the control similar compounds as shown Table 6.

Table 6

| Compound | Active ingredient concentration (p.p.m) | Percentage of healthy seedlings (%) |
|---|---|---|
| (CH$_3$O)$_2$P(=S)—O—[2-chloro-4-methyl-6-nitrophenyl]  (Compound No. (7)) | 500 | 100 |
| (CH$_3$O)$_2$P(=S)—O—[2-bromo-4-methyl-6-nitrophenyl]  (Compound No. (8)) | 500 | 100 |
| (C$_2$H$_5$O)$_2$P(=S)—O—[2-chloro-4-methyl-6-nitrophenyl] * | 500 | 26.7 |
| (C$_2$H$_5$O)$_2$P(=S)—O—[2-bromo-4-methyl-6-nitrophenyl] * | 500 | 20 |
| (CH$_3$O)$_2$P(=O)—O—[2-chloro-4-methyl-6-nitrophenyl] * | 500 | 0 |
| (CH$_3$O)$_2$P(=O)—O—[2-bromo-4-methyl-6-nitrophenyl] * | 500 | 0 |
| (CH$_3$O)$_2$P(=S)—O—[2,6-dichloro-4-nitrophenyl] **** | 500 | 0 |
| (CH$_3$O)$_2$P(=S)—O—[2-chloro-3-methyl-6-nitrophenyl] **** | 500 | 0 |
| (CH$_3$O)$_2$P(=S)—O—[2-chloro-3-methyl-6-nitrophenyl] **** | 500 | 0 |

Table 6-continued

| Compound | Active ingredient concentration (p.p.m) | Percentage of healthy seedlings (%) |
|---|---|---|
| 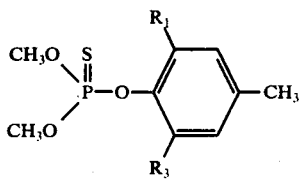 **** | 500 | 0 |
| 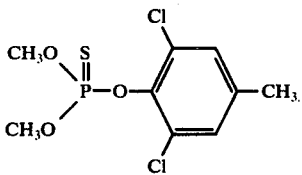 ** | 500 | 0 |
| 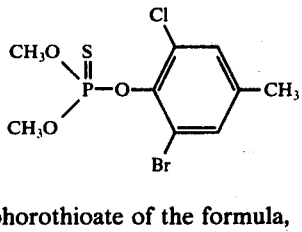 ** | 500 | 0 |
| 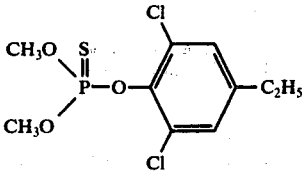 ** | 500 | 0 |
| 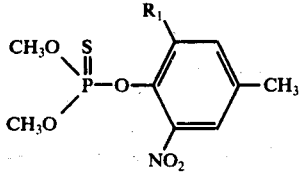 ** | 500 | 0 |
| 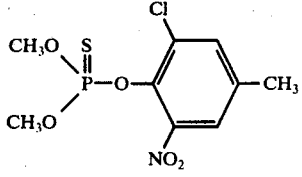 ** | 500 | 0 |
| 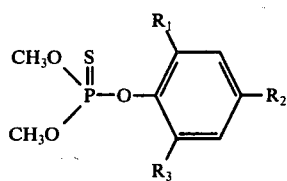 ***** | 500 | 60 |
| Fungus inoculated, Non-treatment | — | 0 |
| Non-inoculation, Non-treatment | — | 100 |

What we claim is:

1. A phosphorothioate of the formula, $$\begin{array}{c} CH_3O\phantom{X}S \\ \phantom{XX}\diagdown\|\phantom{X} \\ \phantom{XXX}P-O-\!\!\!\!\bigcirc\!\!\!\!-R_2 \\ \phantom{X}\diagup \\ CH_3O \end{array} \quad (I)$$

with $R_1$ and $R_3$ on the ring, wherein $R_1$ is a chlorine or bromine atom, $R_2$ is methyl or ethyl group and $R_3$ is a chlorine or bromine atom or nitro group.

2. A soil fungicidal composition including an inert carrier and, as an active ingredient, a fungicidally effective amount of a phosphorothioate of the formula given and defined in claim 1.

3. A phosphorothioate of the formula, $$\begin{array}{c} CH_3O\phantom{X}S \\ \phantom{XX}\diagdown\|\phantom{X} \\ \phantom{XXX}P-O-\!\!\!\!\bigcirc\!\!\!\!-CH_3 \\ \phantom{X}\diagup \\ CH_3O \end{array}$$

with $R_1$ and $R_3$ on the ring, wherein $R_1$ and $R_3$ are as defined in claim 1.

4. A phosphorothioate of the formula, $$\begin{array}{c} CH_3O\phantom{X}S \\ \phantom{XX}\diagdown\|\phantom{X} \\ \phantom{XXX}P-O-\!\!\!\!\bigcirc\!\!\!\!-CH_3 \\ \phantom{X}\diagup \\ CH_3O \end{array}$$

with Cl and Cl on the ring.

5. A phosphorothioate of the formula, $$\begin{array}{c} CH_3O\phantom{X}S \\ \phantom{XX}\diagdown\|\phantom{X} \\ \phantom{XXX}P-O-\!\!\!\!\bigcirc\!\!\!\!-CH_3 \\ \phantom{X}\diagup \\ CH_3O \end{array}$$

with Cl and Br on the ring.

6. A phosphorothioate of the formula, $$\begin{array}{c} CH_3O\phantom{X}S \\ \phantom{XX}\diagdown\|\phantom{X} \\ \phantom{XXX}P-O-\!\!\!\!\bigcirc\!\!\!\!-C_2H_5 \\ \phantom{X}\diagup \\ CH_3O \end{array}$$

with Cl and Cl on the ring.

7. A phosphorothioate of the formula, $$\begin{array}{c} CH_3O\phantom{X}S \\ \phantom{XX}\diagdown\|\phantom{X} \\ \phantom{XXX}P-O-\!\!\!\!\bigcirc\!\!\!\!-CH_3 \\ \phantom{X}\diagup \\ CH_3O \end{array}$$

with $R_1$ and $NO_2$ on the ring, wherein $R_1$ is a chlorine or bromine atom.

8. A phosphorothioate of the formula, $$\begin{array}{c} CH_3O\phantom{X}S \\ \phantom{XX}\diagdown\|\phantom{X} \\ \phantom{XXX}P-O-\!\!\!\!\bigcirc\!\!\!\!-CH_3 \\ \phantom{X}\diagup \\ CH_3O \end{array}$$

with Cl and $NO_2$ on the ring.

9. A soil fungicidal composition according to claim 2, wherein the composition is in the form of a granule, dust, fine granule, wettable powder or emulsifiable concentrate.

* * * * *

UNITED STATES PATENT AND TRADEMARK OFFICE
CERTIFICATE OF CORRECTION

PATENT NO. : 4,039,635
DATED : August 2, 1977
INVENTOR(S) : Toshiro KATO, et al

It is certified that error appears in the above-identified patent and that said Letters Patent are hereby corrected as shown below:

In the Foreign Application Priority Data, the following two priorities claimed were omitted: Japan, Patent Application No. 7400/74 filed on January 14, 1974 and Japan, Patent Application No. 51530/74 filed on May 8, 1974.

Column 2, the formula reading

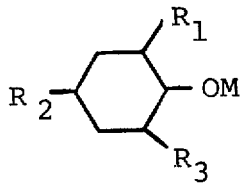       should read       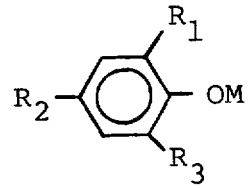

Signed and Sealed this
Eleventh Day of April 1978

[SEAL]

Attest:

RUTH C. MASON
Attesting Officer

LUTRELLE F. PARKER
Acting Commissioner of Patents and Trademarks